(12) United States Patent
Wittenberger et al.

(10) Patent No.: US 9,931,152 B2
(45) Date of Patent: Apr. 3, 2018

(54) DUAL INJECTION TUBE CRYOCATHETER AND METHOD FOR USING SAME

(75) Inventors: Dan Wittenberger, L'ile Bizard (CA); Claudia Lueckge, L'ile Bizard (CA); Miriam Lane, Willsboro, NY (US)

(73) Assignee: Medtronic CryoCath LP, Toronto, Ontario (CA)

( * ) Notice: Subject to any disclaimer, the term of this patent is extended or adjusted under 35 U.S.C. 154(b) by 1691 days.

(21) Appl. No.: 12/844,388

(22) Filed: Jul. 27, 2010

(65) Prior Publication Data

US 2012/0029493 A1 Feb. 2, 2012

(51) Int. Cl.
*A61B 18/02* (2006.01)
*A61B 18/00* (2006.01)
*A61B 90/00* (2016.01)

(52) U.S. Cl.
CPC ...... *A61B 18/02* (2013.01); *A61B 2018/0022* (2013.01); *A61B 2018/00166* (2013.01); *A61B 2018/00642* (2013.01); *A61B 2018/0212* (2013.01); *A61B 2090/064* (2016.02)

(58) Field of Classification Search
CPC ............ A61B 18/02; A61B 2018/0262; A61B 2018/2012
USPC ...................................... 606/20–26
See application file for complete search history.

(56) References Cited

U.S. PATENT DOCUMENTS

| 3,613,689 A | 10/1971 | Crump et al. |
| 5,139,496 A | 8/1992 | Hed |
| 5,423,807 A | 6/1995 | Milder |
| 6,241,722 B1 | 6/2001 | Dobak et al. |
| 6,551,274 B2 | 4/2003 | Heiner |
| 6,949,094 B2* | 9/2005 | Yaron ............................. 606/21 |
| 7,449,018 B2 | 11/2008 | Kramer |
| 2002/0045892 A1 | 4/2002 | Kramer |
| 2007/0250050 A1* | 10/2007 | Lafontaine ..................... 606/21 |

(Continued)

FOREIGN PATENT DOCUMENTS

WO 9927862 A1 6/1999

OTHER PUBLICATIONS

United States Patent Office Certificate of Correction for U.S. Pat. No. 3,613,689, dated Oct. 19, 1971, 1 page.

(Continued)

*Primary Examiner* — John R Downey
(74) *Attorney, Agent, or Firm* — Christopher & Weisberg P.A.

(57) ABSTRACT

A medical device includes a catheter body having a first injection lumen, a second injection lumen, and an exhaust lumen, where the first injection lumen provides a fluid flow rate greater than a fluid flow rate provided by the second injection lumen; an expandable element coupled to the catheter body in fluid communication with the first and second injection lumens; a cryogenic fluid source in fluid communication with the first and second injection lumens; a valve in fluid communication with the first and second injection lumens to selectively allow fluid flow to at least one of the first and second injection lumens; a pressure sensor in fluid communication with an interior defined by the expandable element; and a controller in communication with the pressure sensor programmed to regulate fluid flow through the first injection lumen based at least in part on a signal from the pressure sensor.

17 Claims, 3 Drawing Sheets

(56) References Cited

U.S. PATENT DOCUMENTS

2009/0299355 A1  12/2009  Bencini et al.

OTHER PUBLICATIONS

Communication pursuant to Article 94(3) EPC, dated Aug. 30, 2017, corresponding European Application No. 11 738 907.2-1666, 4 pages.

* cited by examiner

DUAL INJECTION TUBE CRYOCATHETER AND METHOD FOR USING SAME

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for tissue treatment, and in particular, towards systems and methods of use thereof for mapping and thermally ablating cardiac tissue.

BACKGROUND OF THE INVENTION

Electrophysiological procedures often involve recording cardiac electrical activity to determine the location of arrhythmogenic tissue causing heart rhythm abnormalities, such as atrial fibrillation, atrial flutter, ventricular arrhythmias, atrial-ventricular (AV) conduction delays or blocks, and paroxysmal supraventricular tachycardia (PSVT), for example. Treatment of such arrhythmias typically include diagnosing the source of the arrhythmia by locating its origin ("mapping") and restoring normal heart rhythms by isolating or destroying the arrhythmia-causing sites ("ablation").

Today, many electrophysiological medical procedures, including those involving cardiac diagnoses and treatments, are performed using minimally invasive surgical techniques, wherein one or more slender implements such as catheters or the like are inserted through small incisions into a patient's body. For ablation procedures, the treatment implement or device can include a rigid or flexible structure having an ablation implement at or near its distal end placed adjacent to the tissue to be ablated. Tissue ablation is typically undergone to thermally destroy or surgically remove arrhythmia-causing tissue. Such thermal techniques often include burning or freezing the arrhythmogenic focus or conduction defect and thus destroying the offending tissue region or structure. While radio frequency (RF) energy is a popular method for ablation, once a physician commences RF energy delivery to the subject tissue, the procedure is irreversible. No correction can be made for mapping or errors in identifying the origin of the arrhythmia.

Cooling the target tissue to a certain degree, however, does allow for the temporary interruption of electrical activity proximate such tissue. The resulting effects on the heart may then be measured, as with the mapping techniques outlined above, to confirm that the temporarily-stunned tissue is indeed the unwanted tissue that should subsequently be permanently ablated. Tissue temperatures in the range of approximately +10 to −40 degrees Celsius may be used for relatively short periods of time to cause a reversible interruption of electrical activity in either normal or arrhythmic tissue. This range may be used with mapping techniques to confirm the effects of cryotreatment and to assess heart function. Tissue temperatures less than approximately −40 degrees Celsius may be used to cause permanent interruption of electrical activity, cell death, necrosis, or apoptosis in some or all of the tissues surrounding the target region of tissue.

In light of the varied temperatures that can be provided through cryotreatment to either temporarily stun the tissue or permanently ablate the target tissue, it would be desirable to provide for the efficient and controllable operation and regulation of a cryogenic device employed for these purposes.

SUMMARY OF THE INVENTION

The present invention advantageously provides a method and system for the efficient and controllable operation and regulation of a cryogenic device employed for cryotreatment to either temporarily stun the tissue or permanently ablate the target tissue. In particular, a medical device is disclosed, having an elongate body; a first injection lumen disposed in the elongate body; a second injection lumen disposed in the elongate body and independently operable from the first injection lumen; and an exhaust lumen disposed in the elongate body. The second injection lumen may define a fluid flow rate capability less than a fluid flow rate capability defined by the first injection lumen, for example, the second injection lumen can define a cross-sectional diameter less than a cross-sectional diameter defined by the first injection lumen. The device may include an expandable element coupled to the elongate body in fluid communication with the first and second injection lumens and a cryogenic fluid source in fluid communication with at least one of the first and second injection lumens. A valve may be included in fluid communication with the first and second injection lumens to selectively allow fluid flow to at least one of the first and second injection lumens. The device may include a pressure sensor in fluid communication with the first injection lumen, and a controller in communication with the pressure sensor, where the controller is programmed to regulate fluid flow through the first injection lumen based at least in part on a signal from the pressure sensor.

A medical device is also provided, having a catheter body having a first injection lumen, a second injection lumen, and an exhaust lumen, where the first injection lumen provides a fluid flow rate greater than a fluid flow rate provided by the second injection lumen; and an expandable element coupled to the catheter body in fluid communication with the first and second injection lumens. The first injection lumen may define a first opening and the second injection lumen may define a second opening, with the first opening being larger than the second opening.

A method of treating tissue is provided, including positioning a distal portion of a medical device proximate a target tissue area, such as cardiac tissue; delivering a coolant to the distal portion through a first injection lumen at a first flow rate; delivering a coolant to the distal portion through a second injection lumen at a second flow rate greater than the first flow rate; and ablating the target tissue area with the distal portion. The method may include measuring a pressure at the distal portion and regulating the delivery of coolant through the second injection lumen based at least in part on the measured pressure, and terminating coolant delivery through the first injection lumen prior to delivering coolant through the second injection lumen. The method may also include sensing an electrical signal of the target tissue area, regulating the delivery of coolant through the first injection lumen to achieve a first temperature at the distal portion; and regulating the delivery of coolant through the second injection lumen to achieve a second temperature at the distal portion lower than the first temperature.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION OF THE INVENTION

Figure 1:
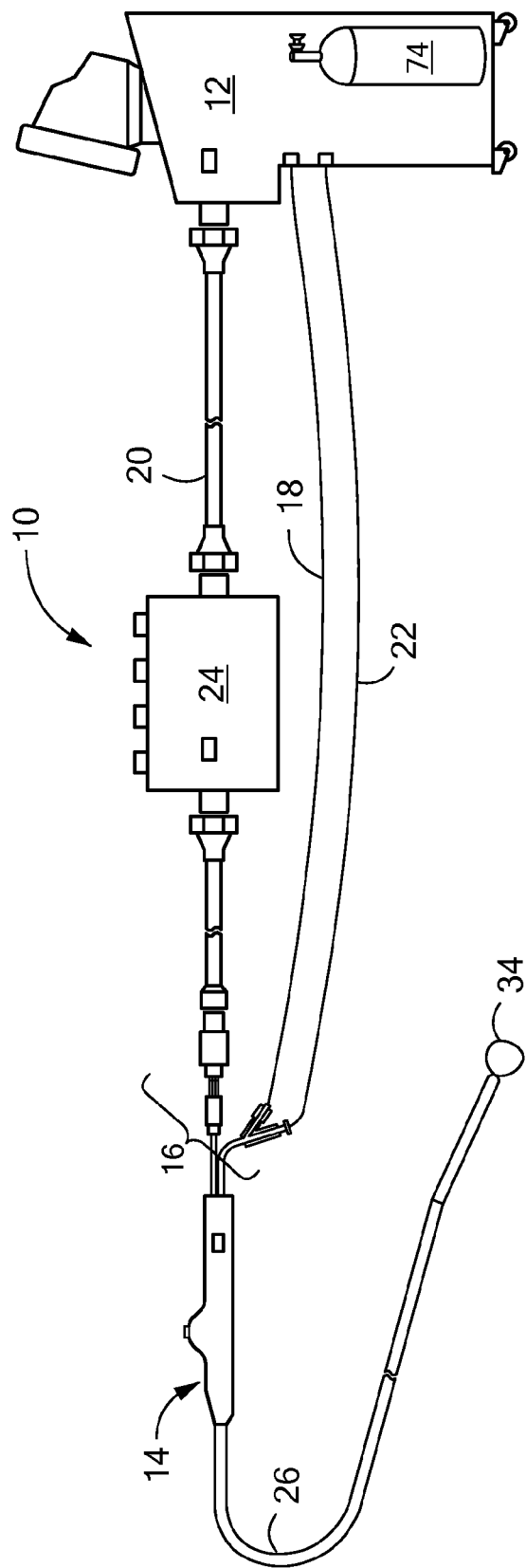
FIG. 1 is an illustration of an embodiment of a medical system constructed in accordance with the principles of the present invention.

The present invention advantageously provides a medical system having improved ability to provide thermal treatment or cycles of varying controlled intensity and/or temperature. Referring now to the drawing figures in which like reference designations refer to like elements, an embodiment of a medical system constructed in accordance with principles of the present invention is shown in FIG. 1 and generally designated as "10." The system generally includes a control unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including cardiac tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial umbilical 18, an electrical umbilical 20 and a vacuum umbilical 22. Although separate umbilicals are shown, it is contemplated that one or more connections may be included in one or more umbilicals having one or more coaxial or otherwise integrally contained passages or conduits therethrough providing electrical and fluid communication between the medical device 14 and the console 12. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture and remove air or blood leaking into the outer vacuum system when portions of the device are outside or inside the patient, respectively.

Figure 2:
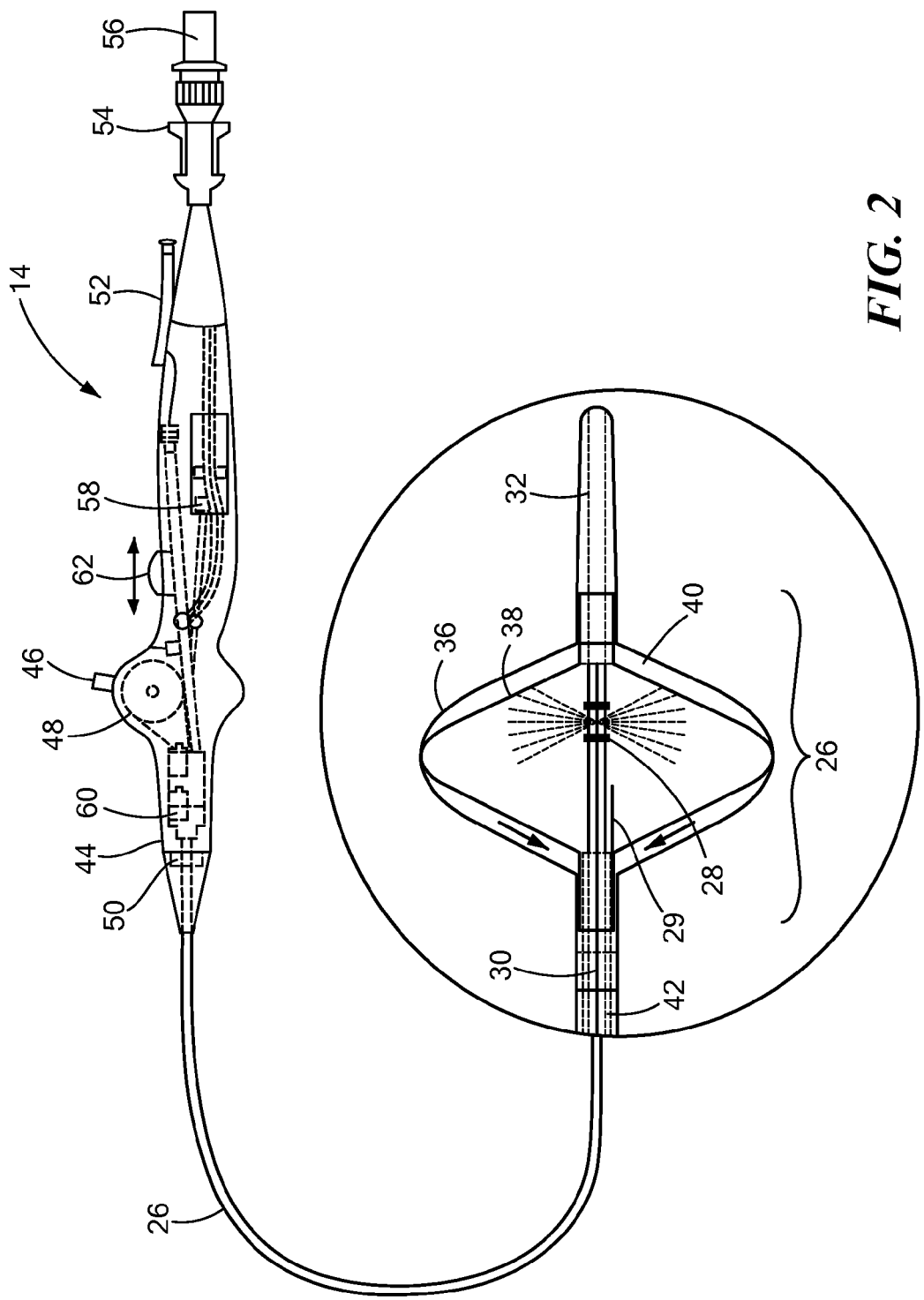
FIG. 2 is an illustration of an embodiment of a medical device constructed in accordance with the principles of the present invention.

Now referring to FIG. 2, the medical device 14 is shown in more detail. The medical device 10 may include an elongate body 26 passable through a patient's vasculature. The elongate body 26 may define a proximal portion and a distal portion, and may further include one or more lumens disposed within the elongate body 26 thereby providing mechanical, electrical, and/or fluid communication between the proximal portion of the elongate body 26 and the distal portion of the elongate body 26. For example, the elongate body 26 may include a first injection lumen 28, a second injection lumen 29 and an exhaust lumen 30 defining fluid flow paths therethrough. The first and second injection lumens may define different dimensions or fluid flow features resulting in differentiated fluid flow characteristics when the respective injection lumens are in use. For example, the first injection lumen 28 may define a larger cross-sectional area or other physical characteristic resulting in a larger fluid flow rate capacity as compared to the dimensions and/or fluid flow rate capacity of the second injection lumen 29. For example, the first injection lumen can have a cross section that is larger than the second injection lumen with diameter ratios ranging from 1.2/1 to 10/1. As an additional example, one or more fluid outlets or apertures defined by the first injection lumen 28 may have a larger area compared to an area defined by one or more fluid outlets or apertures of the second injection lumen 29. These differentiated fluid flow characteristics may allow the injection lumens to be independently operated to for separate, discrete therapeutic or thermal delivery procedures, as described in more detail below.

The elongate body 26 may also include a guidewire lumen 32 movably disposed within and/or extending along at least a portion of the length of the elongate body 26 for over-the-wire applications. The guidewire lumen 32 may define a proximal end and a distal end, and the guidewire lumen 32 may be movably disposed within the elongate body 26 such that the distal end of the guidewire lumen 32 extends beyond and out of the distal portion of the elongate body 26.

The medical device may include one or more treatment regions for energetic or other therapeutic interaction between the medical device 14 and a treatment site. The treatment regions may deliver, for example, radiofrequency energy, cryogenic therapy, or the like to a tissue area in proximity to the treatment region(s). For example, the device 14 may include a first treatment region 34 having a thermal treatment element, such as an expandable membrane or balloon and/or one or more electrodes or other thermally-transmissive components, at least partially disposed on the elongate catheter body. In a particular example, the first treatment region 34 may include a first expandable/inflatable element or balloon 36 defining a proximal end coupled to the distal portion of the elongate body 26 of the medical device 14, while further defining a distal end coupled to the distal end of the guidewire lumen 32. As such, due to the movable nature of the guidewire lumen 32 about the elongate body 26, any axial and/or longitudinal movement of the guidewire lumen 32 may act to tension or loosen the first expandable element 36, i.e., extend or retract the expandable element 36 from a lengthened state to a shortened state during an inflation or deflation thereof. In addition, the first expandable element 36 may have any of a myriad of shapes, and may further include one or more material layers providing for puncture resistance, radiopacity, or the like. The first expandable element 36 may be in communication with the fluid injection and exhaust lumens of the medical device 14 as described above.

The medical device 14 may further include a second expandable/inflatable element or balloon 38 contained within or otherwise encompassed by the first expandable element 36 such that an interstitial region, envelope or space 40 is defined therebetween. The second expandable element 38 may be in communication with the fluid injection and exhaust lumens of the medical device 14 as described above, i.e., a first fluid flow path may provide an inflation fluid or coolant, such as a cryogenic fluid or the like, to the interior of the second expandable element 38. Further, the interstitial region 40 may be in fluid communication with an interstitial lumen 42 providing an auxiliary fluid flow path or avenue separate and independent from a fluid flow path delivering fluid or otherwise in communication with an interior of the second expandable element 38. The second, auxiliary pathway provides an alternate exhaust route for fluid that may leak from the interior of the second expandable element 38 into the interstitial region 40 or fluid entering the medical device 14 from the exterior. In particular, the isolation of the interstitial lumen 42 from the interior of the second expandable element 38 provides an alternate route for fluid to circulate in the case of a rupture or leak of either the first or second expandable elements, as well as allowing for the injection or circulation of fluids within the interstitial region 40 independently of fluids directed towards the second expandable element 38. Towards that end, the interstitial region may be in fluid communication with a fluid source, a vacuum source, or the like separate from a fluid source, vacuum source or otherwise in fluid communication with the interior of the second expandable element 38. Alternatively, the interstitial lumen 42 may be joined to or otherwise in fluid communication with the injection lumen 28 and the interior of the second expandable element 38 to provide a single exhaust or vacuum source for the medical device 14.

Continuing to refer to FIG. 2, the medical device 14 may include a handle 44 coupled to the proximal portion of the elongate body 26, where the handle 44 may include an element such as a lever or knob 46 for manipulating the catheter body and/or additional components of the medical device 14. For example, a pull wire 48 with a proximal end and a distal end may have its distal end anchored to the elongate body 26 at or near the distal end. The proximal end of the pull wire 48 may be anchored to an element such as a cam in communication with and responsive to the lever 46.

The handle 44 can further include circuitry for identification and/or use in controlling of the medical device 14 or another component of the system. The medical device 14 may further include one or more temperature and/or pressure sensors (not shown) proximate the treatment region(s) for monitoring, recording or otherwise conveying measurements of conditions within the medical device 14 or the ambient environment at the distal portion of the medical device 14. The sensor(s) may be in communication with the console 12 for initiating or triggering one or more alerts or therapeutic delivery modifications during operation of the medical device 14. For example, the medical device 14 may include one or more pressure sensors 50 to monitor the fluid pressure within one or more regions and/or fluid flow paths of the medical device 14. The pressure sensor 50 may be used to measure or monitor the pressure within the expandable elements, the fluid injection lumens, and/or the exhaust lumen. Further, although illustrated in FIG. 2 as residing in the handle 44 of the medical device 14, the pressure sensor 60 may be placed within the expandable elements, in direct fluid communication with a portion of the first or second injection lumens, or may also be contained within a portion of the console 12.

Additionally, the handle may be provided with a fitting 52 for receiving a guidewire that may be passed into the guidewire lumen 32. The handle 44 may also include connectors that are matable directly to a fluid supply/exhaust and control unit or indirectly by way of one or more umbilicals. For example, the handle may be provided with a first connector 54 that is matable with the co-axial fluid umbilical 18 and a second connector 56 that is matable with the electrical umbilical 20. The handle 44 may further include blood detection circuitry 58 in fluid and/or optical communication with the injection, exhaust and/or interstitial lumens. The handle 44 may also include a pressure relief valve 60 in fluid communication with the injection, exhaust and/or interstitial lumens to automatically open under a predetermined threshold value in the event that value is exceeded.

Continuing to refer to FIG. 2, the medical device 14 may include an actuator element 62 that is movably coupled to the proximal portion of the elongate body 26 and/or the handle 44. The actuator element 62 may further be coupled to the proximal portion of the guidewire lumen 32 such that manipulating the actuator element 62 in a longitudinal direction causes the guidewire lumen 32 to slide towards either of the proximal or distal portions of the elongate body 26. As a portion of either and/or both the first and second expandable elements 36, 38 may be coupled to the guidewire lumen 32, manipulation of the actuator element 62 may further cause the expandable element(s) to be tensioned or loosened, depending on the direction of movement of the actuator element 62, and thus, the guidewire lumen 32. Accordingly, the actuator element 62 may be used to provide tension on the expandable element(s) 36, 38 during a particular duration of use of the medical device 14, such as during a deflation sequence, for example. The actuator element 62 may include a thumb-slide, a push-button, a rotating lever, or other mechanical structure for providing a movable coupling to the elongate body 26, the handle 44, and/or the guidewire lumen 32. Moreover, the actuator element 62 may be movably coupled to the handle 44 such that the actuator element 62 is movable into individual, distinct positions, and is able to be releasably secured in any one of the distinct positions.

Turning again to FIG. 1, in an exemplary system, a fluid supply 74 including a coolant, cryogenic refrigerant, or the like, an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 44, the elongate body 26, and treatment region 34 of the medical device 14. A vacuum pump in the console 12 may create a low-pressure environment in one or more conduits within the medical device 14 so that fluid is drawn into the conduit(s) of the elongate body 26, away from the treatment region 34 and towards the proximal end of the elongate body 26.

Figure 3:
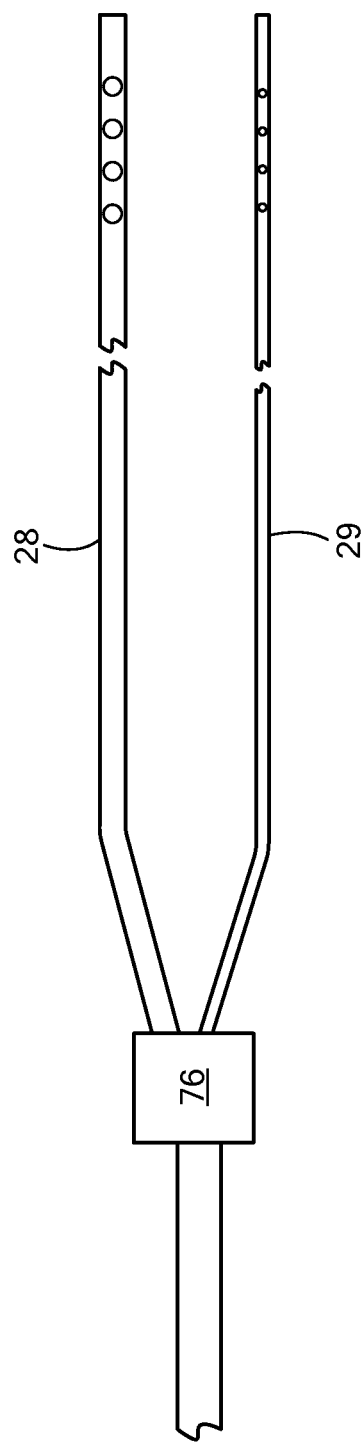
FIG. 3 is an illustration of an injection lumen configuration for the medical device shown in FIG. 2.

The console 12 may include one or more fluid control components including valves, controllers, processors, and/or software modules containing instructions or algorithms to provide for the automated operation and performance of the features, sequences, or procedures described herein. For example, the console 12 and/or the medical device 14 may include one or more valves, controllers, or the like may provide for the controlled, independent, and/or separate dispersion or circulation of fluid through the injection lumens/fluid paths. As shown in FIG. 3, a fluid control element 76 may be in fluid communication with the first and second injection lumens 28, 29 for regulating fluid flow through either and/or both of the lumens. The fluid control element 76 may include a 3-way valve connecting an input segment to either the first injection lumen 28 or second injection lumen 29. Alternatively, the fluid control element 76 may only affect fluid flow to the first injection lumen 28, e.g., a shutoff valve that obstructs fluid delivery to the first injection lumen 28 when closed, while fluid flow to the second injection lumen 29 remains unaffected. In such a configuration, fluid flow may be directed through the second injection lumen 29 unimpeded regardless of the position or state of the fluid control element 76, but when the fluid control element 76 is open to allow fluid flow to the first injection lumen 28, fluid flow through the second injection lumen 29 may substantially decrease because of the larger flow path provided by the first injection lumen 28.

The fluid control element 76 may reside in the handle 44 of the medical device 14, which allows for a single fluid injection or delivery umbilical to connect the medical device to the console 12 and diverting or otherwise regulating flow through the first and second injection lumens in the medical device 14 itself. Alternatively, the fluid control element 76 and separation between the first and second fluid injection lumens 28, 29 may reside in the console. The fluid control element may be in communication with or otherwise include a controller that allows for the selective operation of the fluid control element 76 such that the fluid control element 76, and the resulting fluid flow to the first and second injection lumens, can be controlled, regulated, and/or altogether terminated in response to user inputs, sensor feedback (responsive to a signal from the pressure sensor 50, for example) and/or automatic programming sequences of the system 10.

In an exemplary method of use, the medical system 10 may be used in the cryogenic treatment of targeted tissue. For example, the medical device 14 may be positioned and operated to thermally treat or ablate a targeted tissue region in the heart. The distal portion of the device 14, such as the first treatment region 34, may be positioned adjacent to or in proximity of tissue to be treated. The targeted tissue site may include cardiac tissue that has been mapped for aberrant electrical activity believed to be the source of or otherwise contributing to an arrhythmogenic condition of a patient. The medical device 14 may be used to cool the tissue to a sufficient degree to reversibly stun or otherwise inhibit electrical conduction to confirm the propriety of further treatment at the identified site.

In particular, coolant may be delivered from the coolant source/fluid supply 74 through the second injection lumen 29 to the first treatment element 34. The fluid delivery or circulation through the second injection lumen 29 may include the operation or manipulation of the fluid control element 76 to obstruct fluid from flowing into the first injection lumen 28. The smaller flow rate provided by the second injection tube 29 (compared to that of the first injection tube 28) reduces the amount of coolant delivered to the first treatment element 34, and thus, the resulting reversible, temporarily-induced cryomapping temperature is higher than it would otherwise be with the increased coolant delivery through the first injection lumen 28 for ablation. The smaller injection lumen 29 provides for efficient delivery of a reduced amount of coolant, thus conserving cooling fluid resources of the system, and may reduce or altogether eliminate the need for additional complex control mechanisms to regulate fluid delivery through the second injection lumen 29 to avoid reaching temperatures that would cause permanent tissue destruction.

When the desired cryomapping/reversible cooling procedures using the second injection lumen 29 is completed and tissue has been confirmed for ablation, fluid may be delivered through the first injection lumen 28 and into the treatment region 34. The larger fluid delivery capacity of the first injection lumen 28 compared to the second injection lumen 29 allows for increased cooling power and lower temperatures of the treatment region 34 in order to affect the desired ablation. The fluid delivery through the first injection lumen may include the operation or manipulation of the fluid control element 76 to obtain the desired fluid flow characteristics and resulting temperature of the treatment region 34. Moreover, the fluid flow through the first injection lumen 28 may involve regulation of the fluid control element 76 in response to one or more measured parameters, such as a pressure level indicated by the pressure sensor 50.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
    an elongate body;
    an expandable element coupled to the elongate body;
    a bifurcated coolant injection lumen having a first linear segment disposed in and in fluid communication with the expandable element and defining a first plurality of apertures and having a first cross-sectional diameter, the bifurcated coolant injection lumen further having a second linear segment disposed in and in fluid communication with the expandable element and defining a second plurality of apertures and having a second cross-sectional diameter, the first cross-sectional diameter being greater than the second cross-sectional diameter; and
    an exhaust lumen disposed in the elongate body.

2. The medical device of claim 1, wherein the second coolant injection lumen defines a fluid flow rate capability less than a fluid flow rate capability defined by the first coolant injection lumen.

3. The medical device of claim 1, further comprising a cryogenic fluid source in fluid communication with at least one of the first and second coolant injection lumens.

4. The medical device of claim 1, further comprising a valve in fluid communication with the first and second coolant injection lumens to selectively allow fluid flow to at least one of the first and second coolant injection lumens.

5. The medical device of claim 1, further comprising a pressure sensor in fluid communication with the first coolant injection lumen.

6. The medical device of claim 5, further comprising a controller in communication with the pressure sensor, the controller programmed to regulate fluid flow through the first coolant injection lumen based at least in part on a signal from the pressure sensor.

7. A medical device, comprising:
    a catheter body having a bifurcated injection lumen including a first segment defining a first plurality of apertures each having a first diameter, a second segment defining a second plurality of apertures each having a second diameter, and an exhaust lumen, the first segment providing a fluid flow rate greater than a fluid flow rate provided by the second segment and the first diameter of each of the first plurality of apertures being greater than the second diameter of each of the second plurality of apertures;

a valve in fluid communication with the first and second segments to selectively allow fluid flow from a cryogenic fluid source to at least one of the first and second segments; and an expandable element coupled to the catheter body in fluid communication with the first and second coolant injection lumens.

8. The medical device of claim 7, wherein the first injection lumen defines a first opening and the second injection lumen defines a second opening, the first opening being larger than the second opening.

9. The medical device of claim 1, further comprising a pressure sensor in fluid communication with an interior defined by the expandable element.

10. The medical device of claim 9, further comprising a controller in communication with the pressure sensor, the controller programmed to regulate fluid flow through the first injection lumen based at least in part on a signal from the pressure sensor.

11. A method of treating tissue, comprising:
positioning a treatment element of a medical device proximate a target tissue area;
selectively delivering a coolant from a coolant source to the treatment element through a first linear segment of a bifurcated injection lumen, the first linear segment having a first cross-sectional diameter, the coolant being delivered through the first linear segment at a first flow rate causing the treatment element to reach a non-ablation temperature;
mapping the target tissue area with the treatment element;
selectively delivering the coolant from the coolant source to the treatment element through a second linear segment of the bifurcated injection lumen, the second linear segment having a second cross-sectional diameter that is greater than the first cross-sectional diameter, the coolant being delivered through the second linear segment at a second flow rate greater than the first flow rate, the second flow rate causing the treatment element to reach an ablation temperature; and
ablating the target tissue area with the treatment element.

12. The method of claim 11, further comprising measuring a pressure at the distal portion and regulating the delivery of coolant through the second injection lumen based at least in part on the measured pressure.

13. The method of claim 11, further comprising terminating coolant delivery through the first injection lumen prior to delivering coolant through the second injection lumen.

14. The method of claim 11, further comprising sensing an electrical signal of the target tissue area.

15. The method of claim 11, wherein the target tissue region includes cardiac tissue.

16. The medical device of claim 1, wherein the first coolant injection lumen and the second coolant injection lumen are non-coaxial with each other.

17. The medical device of claim 7, wherein the first injection lumen and the second injection lumen are non-coaxial with each other.

* * * * *